US00PP17745P3

(12) United States Plant Patent
Pieters

(10) Patent No.: US PP17,745 P3
(45) Date of Patent: May 22, 2007

(54) ***CHRYSANTHEMUM* PLANT NAMED 'PPP PAD WH05'**

(50) Latin Name: *Chrysanthemum morifolium*
Varietal Denomination: PPP PAD WH05

(75) Inventor: Dirk Pieters, Ooostnieuwkerke (BE)

(73) Assignee: Pieters Plant Production, BVBA a Belgian Corporation, Oosnieuwkerke (BE)

( * ) Notice: Subject to any disclaimer, the term of this patent is extended or adjusted under 35 U.S.C. 154(b) by 158 days.

(21) Appl. No.: 11/115,703

(22) Filed: Apr. 27, 2005

(65) Prior Publication Data

US 2006/0248621 P1 Nov. 2, 2006

(51) Int. Cl.
*A01H 5/00* (2006.01)

(52) U.S. Cl. ..... Plt./288

(58) Field of Classification Search ..... Plt./288
See application file for complete search history.

*Primary Examiner*—Kent Bell
*Assistant Examiner*—Annette H Para
(74) *Attorney, Agent, or Firm*—Albert O. Cota

(57) ABSTRACT

A new and distinct *Chrysanthemum* plant cultivar is disclosed, characterized by large decorative type inflorescences, consistent flowering response to short days, blooming consistently after 49 days of short day length, white ray florets, free branching habit, and a consistent natural season flowering habit during the first week of September.

1 Drawing Sheet

Figure 1:
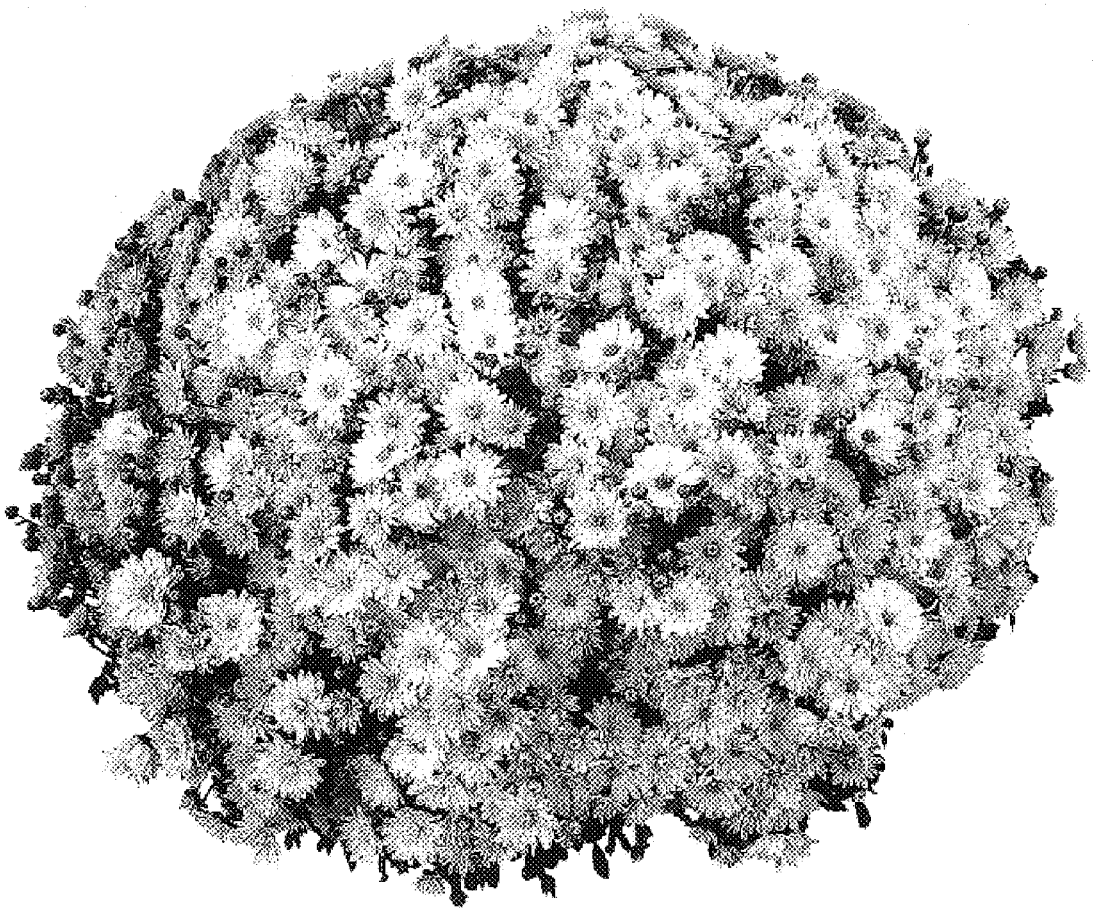

Latin name of the genus and species: *Chrysanthemum morifolium.*
Variety denomination: 'PPP PAD WH05'.

BACKGROUND OF THE INVENTION

The new cultivar 'PPP PAD WH05' is a product of an induced mutation of the parent *Chrysanthemum* plant variety 'GEDI TWO PAD' (U.S. Plant Pat. No. 14,501) using gamma ray treatment at a dose of 20 Gy. The new cultivar was discovered and selected by Dirk Pieters in September 2002 in Oostnieuwkerke, Belgium.

Asexual reproduction of the new cultivar 'PPP PAD WH05' by terminal cuttings and tissue culture was performed in Oostnieuwkerke, Belgium, and has shown that the unique features of this new cultivar are stable and reproduced true to type on successive generations.

SUMMARY OF THE INVENTION

The cultivar 'PPP PAD WH05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP PAD WH05'. These characteristics in combination distinguish 'PPP PAD WH05' as a new and distinct *Chrysanthemum* cultivar:

1. Large decorative type inflorescence;
2. Consistent flowering response to short days, blooming consistently after 49 days of short day length;
3. Free branching habit; and 4. Consistent natural season flowering habit during the first week of September.

Plants of the new cultivar are similar to plants of the parent variety, 'GEDI TWO PAD,' in most horticultural characteristics, however the new cultivar 'PPP PAD WH05' is shorter than the parent and has more ray florets. Additionally, the new variety 'PPP PAD WH05' has different color ray florets than the parent 'GEDI TWO PAD' and has a more apparent disc than the parent.

In comparison to the commercially available variety 'GEDI ONE TER' (U.S. Plant Pat. No. 13,885), 'PPP PAD WH05' shows disc florets with age. Additionally, the new variety 'PPP PAD WH05' naturally blooms one week later than the comparable variety. Further, the new variety 'PPP PAD WH05' has more inflorescence per flowering branch and has less ray florets per inflorescence than the comparable variety 'GEDI ONE TER.'

BRIEF DESCRIPTION OF THE PHOTOGRAPH

The accompanying photograph in FIG. 1 illustrates in full color a typical plant of 'PPP PAD WH05' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP PAD WH05' plants grown in Oxnard, Ventura County, Calif., during the month of September 2004. The growing temperature ranged from 12° C. to 15° C. at night to 12° C.

to 20° C. during the day. Measurements and numerical values represent averages of typical flowering types.

Botanical classification: *Chrysanthemum morifolium* cultivar 'PPP PAD WH05'.
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 28 cm.
Plant spread: Approximately 32 cm.
Growth rate: Moderate.
Branching characteristics: Free Branching.
Length of lateral branches: Approximately 25 cm.
Number of leaves per lateral branch: Approximately 20.
Age of plant described: Approximately 146 days.

FOLIAGE

Leaf:
- *Arrangement.*—Alternate single.
- *Average length.*—Approximately 5.4 cm.
- *Average width.*—Approximately 3.5 cm.
- *Shape of blade.*—Ovate.
- *Apex.*—Acuminate.
- *Base.*—Attenuate.
- *Attachment.*—Stalked.
- *Margin.*—Serrate.
- *Texture of top surface.*—Lightly pubescent.
- *Texture of bottom surface.*—Lightly pubescent.
- *Leaf internode length.*—Approximately 1.2 cm.
- *Color.*—Young foliage upper side: Near Green 137A. Young foliage under side: Near Green 138A. Mature foliage upper side: Near Green 138A. Mature foliage under side: Near Green 138A.
- *Venation.*—Type: Palmately net. Venation color upper side: Near Green 138C. Venation color under side: Near Green 138C.

Petiole:
- *Average length.*—Approximately 2.4 cm.
- *Color.*—Near Green 138B.
- *Diameter.*—Approximately 0.8 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the first week in September.
- *Number of inflorescences per lateral branch.*—Approximately 21.
- *Inflorescence diameter.*—Approximately 4.8 cm.
- *Inflorescence depth.*—1.8 cm.
- *Inflorescence longevity on plant.*—Approximately 25 days.
- *Persistence.*—Persistent.

Ray florets:
- *Appearance.*—Matte.
- *Texture.*—Smooth.
- *Average number of ray florets per inflorescence.*—155.
- *Shape.*—Oblanceolate.
- *Aspect.*—Flat.
- *Margin.*—Entire.
- *Apex.*—Obtuse.
- *Length.*—Approximately 2.2 cm.
- *Width.*—Approximately 1 cm.
- *Color.*—Upper surface at first opening: Near White 158D. Upper surface at maturity: Near White 155D. Upper surface at fading: Near White 158C. Under surface at first opening: Near White 155D. Under surface at maturity: Near White 155D. Under surface at fading: Near White 158C.

Disc florets:
- *Appearance.*—Shiny.
- *Texture.*—Smooth.
- *Average number of florets per disc.*—Approximately 20.
- *Shape.*—Cylindric.
- *Apex.*—Obtuse.
- *Average length.*—Approximately 0.7 cm.
- *Average width.*—Approximately 0.2 cm.
- *Color.*—At first opening: Near Yellow 13B. At maturity: Near Yellow 20A. At fading: Near Yellow 22A.

Peduncle:
- *Length.*—At terminal end (shortest): Approximately 3.7 cm. At lateral end (longest): Approximately 7.7 cm.
- *Angle to stem.*—Acute.
- *Strength.*—Moderate.
- *Color.*—Near Green 137C.
- *Habit.*—Upright.
- *Diameter.*—4 cm.
- *Surface texture.*—Lightly pubescent.

Inflorescence bud:
- *Length.*—Approximately 1 cm.
- *Diameter.*—Approximately 1 cm.
- *Form.*—Globular.
- *Color.*—Near Yellow Orange 20D.

Involucral bracts (phyllaries):
- *Appearance.*—Matte.
- *Texture.*—Lightly pubescent.
- *Number.*—Approximately 20.
- *Shape.*—Ovate.
- *Margin.*—Entire.
- *Apex.*—Acute.
- *Length.*—1 cm.
- *Width.*—0.8 cm.
- *Color.*—Upper side: Near Green 137A. Under side: Near Green 137A.

REPRODUCTIVE ORGANS

Ray florets:
- *Number of pistils per floret.*—1.
- *Stigma shape.*—2 branched.
- *Stigma color.*—Near Yellow 17C.
- *Style color.*—Near Yellow 2B.
- *Style length.*—0.6 cm.
- *Stamens.*—Absent.

Disc florets:
- *Number of pistils per floret.*—1.
- *Stigma shape.*—Cylindric.
- *Stigma color.*—Near Yellow 13B.
- *Style length.*—0.5 cm.
- *Style color.*—Near Yellow Green 154A.
- *Number of stamens per floret.*—Approximately 5.

*Anther shape.*—Tubular.
*Anther color.*—Near Yellow 13A.
*Pollen color.*—Near Yellow 15A.

OTHER CHARACTERISTICS

Disease resistance: Neither resistance nor susceptibility to diseases or pests has been observed in this variety.

Drought tolerance/ cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP PAD WH05' as herein illustrated and described.

* * * * *